United States Patent

Bialosky et al.

[11] Patent Number: 6,090,832
[45] Date of Patent: Jul. 18, 2000

[54] PROCESS FOR MAKING ANTIMICROBIAL AGENTS IN AQUEOUS DISPERSION FORM CONTAINING 2-(4-THIAZOLYL)-BENZIMIDAZOLE ALONE OR IN COMBINATION WITH 1,2-DIBROMO-2,4-DICYANOBUTANE

[75] Inventors: David H. Bialosky, Pittsburgh; Jodi L. Martin, Imperial, both of Pa.

[73] Assignee: Calgon Corporation, Pittsburgh, Pa.

[21] Appl. No.: 08/509,470

[22] Filed: Jul. 31, 1995

[51] Int. Cl.[7] ..................................... A01N 43/78
[52] U.S. Cl. ........................ 514/365; 514/672; 514/777
[58] Field of Search .................... 514/365, 672, 514/777, 781

[56] References Cited

U.S. PATENT DOCUMENTS

| | | |
|---|---|---|
| 3,370,957 | 2/1968 | Wagner et al. . |
| 3,833,731 | 9/1974 | Grier et al. . |
| 3,873,597 | 3/1975 | Harmetz et al. . |
| 3,877,922 | 4/1975 | Grier et al. . |
| 4,442,122 | 4/1984 | Engelhart et al. . |
| 4,496,581 | 1/1985 | Engelhart et al. . |
| 4,830,657 | 5/1989 | Jakubowski et al. . |
| 4,906,648 | 3/1990 | Minami et al. ........................ 514/365 |
| 5,034,405 | 7/1991 | Jakubowski et al. . |
| 5,529,807 | 6/1996 | Burkhart, Jr. et al. ............... 427/372.2 |
| 5,554,373 | 9/1996 | Seabrook et al. ...................... 424/400 |
| 5,744,494 | 4/1998 | McKellar et al. ...................... 514/388 |

FOREIGN PATENT DOCUMENTS

| | | |
|---|---|---|
| 61-103810 | 5/1986 | Japan . |
| 61-225104 | 10/1986 | Japan . |

OTHER PUBLICATIONS

Derwent Database WPI, AN 94–322053 Abstract only, week 94/40 corresponding to JP–A–06 247809 (Shinto Toryo KK).
Chemical Abstracts No. 108559W; vol. 115, No. 11, 1991.
Calgon Corporation Product Bulletin Metasol TK–100®.
Calgon Corporation Product Bulletin Tektamer® 38.
Calgon Corporation Product Bulletin Tektamer® 38AD.

*Primary Examiner*—Robert H. Harrison
*Attorney, Agent, or Firm*—Diane R. Meyers; Eckert Seamans Cherin & Mellott, LLC

[57] ABSTRACT

Aqueous dispersions of 2-(4-thiazolyl)-benzimidazole (TBZ), alone or in combination with 1,2-dibromo-2,4-dicyanobutane (DBDCB), and processes for making the same, are disclosed. These processes generally comprise mixing a xanthan gum with water, adding TBZ and mixing until uniform. DBDCB dispersions are prepared by mixing xanthan gum with water, adding DBDCB, maintaining the mixture at a temperature below about 40° C., grinding the mixture and mixing until uniform. The TBZ and DBDCB dispersions are then blended to prepare a dispersion containing both active ingredients. A method for inhibiting microbial growth utilizing these dispersions is also claimed.

11 Claims, No Drawings

PROCESS FOR MAKING ANTIMICROBIAL AGENTS IN AQUEOUS DISPERSION FORM CONTAINING 2-(4-THIAZOLYL)-BENZIMIDAZOLE ALONE OR IN COMBINATION WITH 1,2-DIBROMO-2,4-DICYANOBUTANE

BACKGROUND OF THE INVENTION

1. Field of the Invention

The present invention relates to processes for preparing aqueous dispersions of designated antimicrobial agents. These dispersions and various uses thereof are also claimed. The present dispersions are generally useful for inhibiting microbial growth in typical media where such microbial growth occurs.

More particularly, the present invention is concerned with processes for making aqueous dispersions of 2-(4-thiazolyl)-benzimidazole, alone or in combination with 1,2-dibromo-2,4-dicyanobutane. These processes rely on the use of xanthan gum to stabilize the dispersions. The present invention also relates to the novel dispersions described herein and to methods of inhibiting microbial growth comprising contacting said growth with an effective amount of the dispersions prepared by the processes herein disclosed.

2. Description of the Background Art

A number of important industries have experienced adverse effects from the activity of biological growth on the raw materials which they employ, in their process waters, on various components of their manufacturing processes, and in the finished products which they produce.

Such industries include, inter alia, the paint, wood, textile, cosmetic, leather, tobacco, fur, rope, paper, pulp, plastics, fuel, oil, rubber and machine industries. In these industries, therefore, it is generally desirable to utilize one or more biocides in an attempt to control microorganism populations. As used herein, the phrases "biocide", "antimicrobial" and "inhibiting microbial growth" describe the killing, inhibition or control of biological growth including but not limited to bacteria, algae and fungi such as yeast, mold and mildew.

Both 2-(4-thiazolyl)-benzimidazole (TBZ), also known as thiabendazole, and related compounds and l,2-dibromo-2,4-dicyanobutane (DBDCB), also known as 2-bromo-2-bromomethyl-glutaronitrile, and related compounds are known in the art as antimicrobial agents, both alone and in combination with other compounds. TBZ is commercially available as a dispersion from Calgon Corporation, Pittsburgh, Pa. and DBDCB is commercially available from Calgon Corporation in dry, organic solution and aqueous dispersion forms.

U.S. Pat. No. 4,830,657 describes a synergistic antimicrobial combination comprising DBDCB and 1,2-benzisothiazolin-3-one.

U.S. Pat. No. 4,442,122 describes the use of 1,2-dibromo-2-cyanoalkane compounds to inhibit microbial growth; this patent also discloses use of these compounds in conjunction with TBZ.

U.S. Pat. No. 4,496,581 describes the use of 1,2-dibromo-2-cyano-2-(heterocyclic) alkane compounds to inhibit microbial growth; this patent also discloses use of these compounds in conjunction with TBZ.

U.S. Pat. No. 5,034,405 describes admixtures of DBDCB, 2-methyl-4-isothiazolin-3-one and 5-chloro-2-methyl-4-isothiazolin-3-one as antimicrobial agents.

U.S. Pat. No. 3,370,957 describes TBZ and related compounds and their use in controlling fungal growth.

DBDCB and related compounds, and their use as antibacterial, antifungal and algicidal agents, are also disclosed in U.S. Pat. Nos. 3,833,731, 3,877,922, and 3,873,597. U.S. Pat. No. 3,833,731 further discloses the use of DBDCB in conjunction with TBZ as an antimicrobial agent; this patent, however, does not disclose an aqueous dispersion containing DBDCB and TBZ which utilizes xanthan gum as a stabilizer.

The xanthan gum based processes of the present invention, the resulting compositions and their use as antimicrobial agents are not known or suggested in the art.

One problem that is commonly experienced with commercially available TBZ dispersions is that they are not compatible with commercially available DBDCB dispersions. Furthermore, standard, commercial TBZ dispersions are often very difficult to meter and handle because of their viscosity. Thus, despite the commercial availability of TBZ and DBDCB dispersions, there remains a need for methods of producing stable aqueous dispersions containing either TBZ alone or TBZ in combination with DBDCB.

It is contemplated that the dispersions prepared by the processes of the present invention will have application in any industrial aqueous system in which inhibition of microbial growth is desired. Important applications are believed to include, inter alia, inhibiting the growth of bacteria in aqueous paints, adhesives, resins, drilling fluids, pigment dispersions, latex emulsions, metal-working fluids and joint cements; controlling mold and mildew growth on natural and synthetic fibers; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g. cardboard and particle board; preventing sap stain discoloration on freshly cut wood of various kinds; controlling bacterial and fungal growth in clay and pigment slurries of various types which are manufactured for later use in paper coating and paint manufacturing, for example, and which are susceptible to degradation by microorganisms during storage and transport; as a hard surface disinfectant to prevent growth of bacteria and fungi on walls, floors, etc.; and in swimming pools, ponds and cooling water systems to prevent algal growth.

An application for which the synergistic dispersion of DBDCB and TBZ as prepared by the processes of the present invention has been found especially useful is in the protection of paint films from attack by fungi. Paint film fungicides which can preserve paint films from the deleterious effects of fungal attack which occur during weathering of the paint film have long been sought. Few, however, have been found due to the stringent requirements for such a successful paint fungicide. Moreover, the ability to provide in-can preservative activity, as well as paint film protection, is also desirable. This additional characteristic is seldom seen in a paint film fungicide. A synergistic admixture of DBDCB and TBZ as prepared according to the methods of the present invention is particularly useful, therefore, in functioning as an all in one in-can preservative and mildewcide.

It is believed that the aqueous TBZ dispersions prepared by the methods of the present invention can be used in any application in which TBZ would be used, assuming that substantial problems with miscibility between the TBZ dispersion and the system being treated do not arise. Likewise, the aqueous dispersion containing blends of DBDCB and TBZ can be used in any application in which use of these two components together would be beneficial; this provides a further advantage in that it allows for the simultaneous feeding of both DBDCB and TBZ in one product at a predetermined, desired ratio. Because the aqueous dispersions prepared according to the processes of the present invention are in a form which is easy to meter and pump, it is anticipated that the improved handling properties of these aqueous dispersions will allow for their use in even more applications than TBZ alone, and TBZ in combination with DBDCB, are currently employed.

SUMMARY OF THE INVENTION

The present invention generally meets the above described needs by providing aqueous dispersions containing antimicrobial agents wherein problems with viscosity and handling, as currently experienced with 2-(4-thiazolyl)-benzimidazole (TBZ) dispersions, are reduced. These novel dispersions, which are stabilized by addition of an effective amount of a xanthan gum, contain TBZ, either alone or in combination with 1,2-dibromo-2,4-dicyanobutane (DBDCB); dispersions containing both TBZ and DBDCB also reduce compatibility problems encountered when commercial TBZ and DBDCB dispersions are combined.

The present invention also provides processes for making these novel aqueous dispersions. Preparation of the TBZ aqueous dispersion includes the steps of mixing an effective amount of xanthan gum with water, adding TBZ to the mixture in an amount effective to give the desired active ingredient concentration and mixing until uniform.

One method for preparing a dispersion containing both DBDCB and TBZ comprises: a) preparing a DBDCB dispersion by mixing an effective amount of xanthan gum with water; adding DBDCB to the mixture in an amount effective to give the desired active ingredient concentration; mixing until uniform; cooling the mixture to a temperature below about 40° C., if the temperature is higher; and grinding the uniform mixture; b) preparing a TBZ dispersion as described above; and c) blending a predetermined amount of each of these dispersions so as to provide a dispersion containing both active ingredients in the desired ratio.

In another embodiment of the present invention, the process for preparing an aqueous dispersion form of a DBDCB and TBZ admixture comprises: a) mixing an effective amount of xanthan gum with water; b) adding DBDCB to the mixture in an amount effective to give the desired active ingredient concentration; c) mixing until uniform and cooling to a temperature below about 40° C., if the temperature is higher; d) grinding the uniform mixture; e) adding TBZ to the ground mixture in an amount effective to give the desired active ingredient concentration; and f) mixing until uniform. Alternatively, the TBZ can be added to the xanthan gum/water mixture at the same time as the DBDCB, i.e. before the grinding step; in this alternative embodiment, both active ingredients would be subject to grinding.

The present invention also provides for the use of the aqueous dispersions disclosed herein to inhibit microbial growth. This use includes methods for inhibiting microbial growth comprising contacting said growth with an effective amount of one of the aqueous dispersions described above.

As used herein the terms "amount effective" and "effective amount" refer to that amount of a compound or product needed to bring about a desired result. For example, adding TBZ and/or DBDCB in an "amount effective" to give the desired active ingredient concentration generally refers to the amount of TBZ and/or DBDCB added to a dispersion to produce an antimicrobial agent capable of achieving a desired level of inhibition of microbial growth; an "effective amount" of xanthan gum added to an aqueous dispersion generally refers to that amount of xanthan gum which gives the dispersion the desired stability.

DETAILED DESCRIPTION OF THE PRESENT INVENTION

The present invention is directed to novel aqueous dispersions of antimicrobial agents containing 2-(4-thiazolyl)-benzimidazole (TBZ), alone or in combination with 1,2-dibromo-2,4-dicyanobutane (DBDCB), and processes for making the same. As discussed above, both TBZ and DBDCB are known in the art as biocides; TBZ is primarily known for its efficacy against fungi, and DBDCB for its efficacy against bacteria, although DBDCB is also reported to be effective against algae and fungi. The use of these two biocides together is also known in the art. The novel processes for producing the present aqueous dispersions of TBZ, alone or in combination with DBDCB, and the dispersions which result from these processes, however, are not known in the art.

More particularly the present invention is directed to a process for preparing a TBZ antimicrobial composition in aqueous dispersion form comprising the steps of mixing an effective amount of xanthan gum with water in a vessel fitted with an agitator, adding an effective amount of TBZ to the xanthan gum/water mixture and mixing until uniform. Further, the present invention is directed to the process for making a TBZ antimicrobial composition as described above further including the steps of preparing a DBDCB antimicrobial composition in aqueous dispersion form by mixing an effective amount of xanthan gum with water in a vessel fitted with an agitator; adding an effective amount of DBDCB to the xanthan gum/water mixture and mixing until uniform; maintaining the xanthan gum/water/DBDCB mixture below a temperature of about 40° C.; grinding the above mixture; and mixing a desired quantity of the TBZ antimicrobial composition with a desired quantity of the DBDCB antimicrobial composition to form an admixture containing both DBDCB and TBZ in aqueous dispersion form.

The present invention is also directed to an aqueous dispersion useful as an antimicrobial agent comprising an effective amount of TBZ as an active ingredient and an effective amount of xanthan gum as a stabilizer. Generally, these dispersions contain between about 0.01 and 2% by weight of xanthan gum, between about 0.1 and 60% by weight of TBZ and the balance water. Further, the present invention is directed to the TBZ antimicrobial agent as described above further comprising an effective amount of DBDCB as an active ingredient. This dispersion, according to the present invention can have a total DBDCB and TBZ active ingredient concentration ranging from about 0.1 to 60% by weight of the total product and can be used in a DBDCB to TBZ ratio of between about 4:1 and 1:4. Generally, these dispersions contain between about 0.01 and 2% by weight of xanthan gum, between about 0.01 and 60% by weight of TBZ, between about 0.01 and 60% by weight of DBDCB and the balance water.

The present invention is also directed to a process for preparing an aqueous dispersion of 1,2-dibromo-2,4-dicyanobutane (DBDCB) and 2-(4-thiazolyl)-benzimidazole (TBZ) comprising the steps of: mixing an effective amount of xanthan gum with water in a vessel fitted with an agitator; adding an effective amount of DBDCB to the water/xanthan gum mixture and mixing until uniform; maintaining the water/xanthan gum/DBDCB mixture below a temperature of about 40° C.; grinding the above mixture; adding an effective amount of TBZ to the ground mixture; and mixing until uniform. Further, the present invention is directed to the above process which comprises adding an effective amount of both DBDCB and TBZ to the water/xanthan gum mixture and wherein the step of adding TBZ after grinding is eliminated.

In addition, the present invention is directed to a method of inhibiting microbial growth comprising contacting said growth with an effective amount of an admixture comprising 1,2-dibromo-2,4-dicyanobutane and 2-(4-thiazolyl)-benzimidazole prepared by the process comprising the steps of: mixing an effective amount of xanthan gum with water in a vessel fitted with an agitator; adding an effective amount of DBDCB to the water/xanthan gum mixture and mixing until uniform; maintaining the water/xanthan gum/DBDCB mixture below a temperature of about 40° C.; grinding the above mixture; adding an effective amount of TBZ to the ground mixture; and mixing until uniform.

As stated above, one embodiment of the present invention is directed to the process for making an antimicrobial agent in aqueous dispersion form containing TBZ as its active ingredient. This process generally involves the steps of mixing an effective amount of xanthan gum with water in a tank or vessel fitted with a jacket and an agitator, adding an effective amount of TBZ to the xanthan gum/water mixture and mixing until uniform. The tank or vessel used is preferably stainless steel or glass lined. A level of agitation sufficient to disperse the solid active ingredient in the carrier is required.

An effective amount of xanthan gum is required. As used here, the term "effective amount" refers to that amount of xanthan gum required to give the dispersion its desired consistency and stability. Generally, to produce about 1000 pounds of the aqueous dispersion, an effective amount of xanthan gum would range from about 0.1 to 20 pounds, more preferably from 1 to 15 pounds and most preferably from about 1 to 10 pounds.

Xanthan gum consists of mannose, glucose and glucuronic acid; each repeating block in the xanthan gum molecule contains five sugar units—two mannose units, two glucose units and one glucuronic acid unit. Xanthan gum is commercially available as a powder from the Kelco Company and the Rhone-Poulenc Company. The powder readily dissolves in both hot and cold water, and results in solutions with high viscosity. Xanthan gum also dissolves in acids and bases. Generally, xanthan gum has excellent stability and the viscosity of solutions containing xanthan gum can remain stable for several months.

While it is preferred that the xanthan gum be food grade and cellulase enzyme free, the grade of xanthan gum employed will depend on the final use of the aqueous dispersion and can be selected based on the needs of the individual user. For example, if the dispersion is to be used as a preservative for paint it would be important that the xanthan gum be cellulase enzyme free because of the destructive effect that the cellulase enzyme has on the modified cellulose often used as a stabilizer in paint. Likewise, if the dispersion is to be used in a formulation to coat paper in contact with foodstuffs, a food grade blend would be desired. Suitable xanthan gums for use in the methods of the present invention are commercially available from the Kelco Co., under the name Kelzan®, or the Rhone-Poulenc, Co.

It is also within the scope of the present invention to utilize other suitable gums, such as guar gum, which result in an aqueous dispersion having the desired consistency and stability. Xanthan gum, however, is preferred.

As will be understood by one skilled in the art, the xanthan gum powder should be added to the water at a steady pace, and should not be added so quickly as to cause gels to form in the finished product. Any industrial, process quality water can be used. Zeolite Softened Water or condensate is preferred.

Following addition of the xanthan gum to water, TBZ should be added in an amount effective to give the desired active ingredient concentration. As will be understood by practitioners of this art, the TBZ should be added at a rate slow enough to avoid the formation of lumps and to prevent any dusting of the TBZ. The mixture should be agitated until the TBZ is well dispersed, which again will be apparent to one skilled in the art. After addition of all of the TBZ, the mixture should be agitated for a time sufficient to ensure formation of a uniform slurry, at least about fifteen minutes and preferably about one hour.

The TBZ used is preferably dispersion grade. That is, the particle size of the TBZ should generally average less than 30 microns. Finely ground TBZ suitable for use in the methods of the present invention is available, for example, from Merck as Metasol® TBZ. If courser TBZ is used as a starting material, however, a grinding step generally must be included in the preparation of the TBZ dispersion. Such a grinding step is described below in reference to the preparation of the DBDCB aqueous dispersion.

Effective amounts of various optional processing aids can also be added during preparation of the TBZ dispersions according to the methods of the present invention. For example, an effective amount of sodium chloride, which functions as a crystal modifier, can be added to the blend to serve as a freeze protector. Preferably between about 1 and 10 pounds of sodium chloride should be added for every 1000 pounds of product, more preferably between about 2 and 7 pounds. An effective amount of ethylenediaminetetraacetic acid (EDTA) in any of its various salt forms, such as disodium EDTA ($Na_2EDTA$), can also be added to the blend to protect against low level iron contamination. EDTA acts as a chelating agent, which serves to tie up or bind any iron which may be present in the final product. Preferably between about 0.1 and 5 pounds of EDTA should be added for every 1000 pounds of product, more preferably between about 0.5 and 1.5 pounds. An effective amount of an anti-foam agent can also be optionally added. The anti-foam agent generally contains some form of silicone, and is primarily added to prevent foaming of the product during processing. An appropriate anti-foam for use in the methods of the present invention is Dow Corning® Antifoam AF Emulsion. Preferably between about 1 and 10 pounds of anti-foam should be added for every 1000 pounds of product, more preferably between about 2 and 5 pounds. In addition, use of an effective amount of a wetting agent is highly recommended. Because the TBZ may be added in powder form, the wetting agent can function to disperse the powder, thereby greatly improving processability. Igepal® CTA 639, available from the Rhone-Poulenc Co., is one such wetting agent suitable for use in the methods of the present invention. Preferably between about 1 and 10 pounds of wetting agent should be added for every 1000 pounds of product, more preferably between about 4 and 6 pounds. Effective amounts of any or all of these processing aids can be used. Determination of an effective amount for the intended purpose is well within the skill of practitioners in this art.

In addition, the TBZ aqueous dispersion of the present invention may require a preservative to prevent bacterial growth. This is necessary because TBZ is generally not effective against bacteria. Any suitable biocide effective against bacteria can be used as the preservative; DBDCB in aqueous dispersion form, for example, is suitable for this purpose. A DBDCB aqueous dispersion can be made according to the methods of the present invention, as discussed below, or can be purchased from Calgon Corporation, Pittsburgh, Pa.

While the amount of active ingredient in the aqueous dispersion can be altered to suit the needs of the user, the weight percent of TBZ generally ranges from about 0.1 to about 60% of the dispersion. The two preferred active ingredient concentrations for an aqueous dispersion form of TBZ according to the present invention range from between about 20% to 30%, preferably about 25%, by weight and between about 45% and 55%, preferably about 50%, by weight. The most preferred active ingredient concentration is about 25% by weight. In addition to being economically attractive, the 25% by weight active formulation has excellent viscosity, handling properties and stability. While all of the TBZ aqueous dispersions produced by the methods of the present invention have greatly improved viscosity and handling properties over the TBZ products currently available, the higher the percent of active ingredient the more viscous and difficult to handle the product. For example, the viscosity of the 25% by weight active formulation will typically be between approximately 1100 and 1700 centipoise (cps) while the viscosity of the 50% by weight active formulation will typically be between approximately 5500 and 6500 cps, when viscosity is measured by a Brookfield RV viscometer using a #5 spindle at 50 rpm.

The xanthan gum-containing TBZ aqueous dispersions prepared by the methods of the present invention, regardless of the active ingredient concentration, are generally stable. That is, the dispersions remain uniformly blended for several months. In addition, freeze-thaw stability of all of the formulations are excellent, with no substantial separation of the product or significant change in viscosity over time. Furthermore, the aqueous dispersions as prepared herein are also chemically stable. That is, the biocidal efficacy does not significantly degrade over time.

In another embodiment of the present invention a dispersion containing both TBZ and DBDCB is made by first preparing a TBZ dispersion as described above, preparing a DBDCB dispersion by mixing an effective amount of xanthan gum with water in a vessel fitted with an agitator, adding an effective amount of DBDCB to the xanthan gum/water mixture, mixing until uniform, cooling the mixture to a temperature below about 40° C., and grinding the xanthan gum/water/DBDCB mixture, and finally mixing the necessary quantities of each of the DBDCB and TBZ dispersions to give a blend of the two biocides in the desired DBDCB to TBZ weight ratio. Preparation of the DBDCB dispersion takes place in substantially the same way as the TBZ dispersion with the following notable exceptions.

Following addition of the xanthan gum to the water, the mixture should be cooled, if necessary, to a temperature of less than about 40° C. Maintaining the mixture at a temperature of between about 20° C. and 30° C. is preferred with a temperature of about 25° C. being most preferred. A jacket or coil can be used to cool the mixture. This cooling step is required because DBDCB melts at a temperature of about 45° C. DBDCB, if melted, can corrode the grinder. For this reason it is preferred that the water mixed with the xanthan gum be room temperature or colder. This helps to ensure that the mixture is below 40° C. before grinding begins, which is important because heat is generated during the grinding step, and might even eliminate the need to cool the mixture during grinding.

DBDCB can be added in wet cake form as well as in dry powder form; both of these formulations are commercially available from Calgon Corporation, Pittsburgh, Pa. When using DBDCB in the wet cake form, i.e. DBDCB with water added, it is necessary to compensate for the fact that because of the water content the wet cake is less than 100% active.

For example, if the wet cake contains DBDCB which is less than 100% active, then more wet cake and less water should be used. The calculations necessary to determine this compensation are well within the ordinary skill of one practicing in the art.

Because the particle size of DBDCB is typically prohibitively large, grinding the mixture of xanthan gum, water and DBDCB is generally necessary. A grinder contained within the vessel itself can be employed for this purpose. Preferably the grinder will be separate from the vessel, and attached thereto by pipes or other means through which the mixture can be fed. If the grinder is inside the vessel, it need only be activated when grinding is necessary. If the grinder is separate, a slow initial feed of the mixture to the grinder is typically best so as to prevent lumps of DBDCB from plugging the grinder feed line; this feed rate can be increased as rapidly as the equipment being used will allow. For example, a large, high power grinder will be able to process the mixture at a faster rate than will a smaller, low power grinder. A high intensity grinder arranged to recirculate the mixture is generally preferred. A Comitrol® Processor with a micro-cut head available from the Urschel Co., a Speco colloid mill and a Premier supermill have all been shown to be adequate grinders for use in the methods of the present invention.

A pump to feed the grinder, a second equivalent vessel or tank into which the mix can be transferred through the grinder, and a screen to filter the product can also be used. Once a smooth rapid flow of slurry is established, a sample of the recirculating product stream can be obtained and screened to be sure the particle size specification desired by the user has been met. The method of performing a screen analysis will be familiar to one having ordinary skill in the art. When a grind meeting the required particle size is obtained, the mix can then be transferred through the grinder to the second mix tank. During transfer to the second tank, passing the product through a course screen to remove any lumps or gels is recommended. The second mix tank should then be agitated for about 30 minutes more to ensure a well blended mixture.

As with the preparation of the TBZ dispersion, the concentration of active ingredient in the DBDCB dispersion can be varied to suit the needs of the user and can range, for example, from between 0.1 and 60% by weight of the total product. Preferred active ingredient concentrations range from between about 20% to 30% by weight of the total product and between about 45% to 55% by weight of the total product; a concentration of about 25% by weight of the total product is most preferred. A preferred wet mesh particle size percentage retained on USS No. 100 mesh is 0.25 maximum and through USS No. 200 mesh 97.5 minimum, and a preferred Brookfield viscosity measured in cps is between about 1400 and 3100 as determined by a Brookfield RV viscometer using a #5 spindle at 50 rpm and at 25° C.; both of these specifications will be understood by one having ordinary skill in the art. It will also be understood by one skilled in the art that the wet mesh particle size and Brookfield viscosity can be varied to suit the needs of the user.

Sodium chloride, EDTA, and an anti-foam agent, as described above in reference to the preparation of the TBZ dispersion, are also suitable processing agents for preparation of the DBDCB dispersion. Adding an anti-foam agent is particularly important during preparation of the DBDCB dispersion to prevent foaming during the grinding step. Addition of the wetting agent, added in preparation of the TBZ dispersion, is not necessary here if adding the DBDCB in wet cake form. A block copolymer surfactant can also optionally be added to improve the freeze/thaw stability of the product; a suitable surfactant for this purpose is Pluronic® F-127 available from the Wyandot Chemical Co. Preferably between about 0.1 and 10 pounds of surfactant should be added for every 1000 pounds of product, more preferably between about 0.5 and 1.5 pounds.

Following the preparation of both the TBZ and the DBDCB aqueous dispersions, an admixture of the two aqueous dispersions containing both active ingredients can then be prepared. The overall active ingredient concentration of the admixture will be dependent on the active ingredient concentration of the TBZ and DBDCB dispersions. For example, if the active ingredient of both of the dispersions is about 25% by weight, the active ingredient concentration of the final blend will similarly be around 25% by weight. As will be appreciated by one skilled in the art, this active concentration can be increased or decreased to suit the needs of the user by altering the amounts of starting ingredients used in preparation of the two dispersions. As discussed above with reference to the TBZ dispersion, the higher the active ingredient the more viscous the product. A viscous product can have numerous handling problems and for this reason a TBZ/DBDCB dispersion having an active concentration of about 25% by weight is preferred.

The ratio of DBDCB to TBZ in the final blend can also be adjusted over a broad range and can be varied as needed by the user. The proportion of the two components in the aqueous dispersion blend are dictated by the desired dosage levels of each component to be employed in each end use application. While it is anticipated that the ratio of DBDCB to TBZ may be chosen to provide a synergistic effect between the two biocides, any ratio of DBDCB to TBZ can be achieved by practicing the methods of the present invention. A DBDCB to TBZ weight ratio between 4:1 and 1:4 on an active basis is preferred, both in terms of the efficacy and synergy of the biocides as well as the economic considerations; a ratio of 4:1 is most preferred.

In another embodiment of the methods of the present invention, there is provided another process for making an aqueous dispersion containing both DBDCB and TBZ, comprising the steps of mixing an effective amount of xanthan gum with water in a vessel fitted with an agitator, adding an effective amount of DBDCB to the xanthan gum/water mixture, cooling the mixture to a temperature below about 40° C. if the temperature is higher, grinding the mixture, adding an effective amount of TBZ to the ground mixture and mixing until uniform, generally at least about 30 minutes. The processing agents described above can optionally be added to the aqueous dispersion here in the same manner.

In an alternative to this embodiment the TBZ can be added to the slurry containing the xanthan gum, water and DBDCB prior to grinding rather than after the grinding. In this alternative, the TBZ is also subjected to the grinding step. In most cases grinding of the TBZ is not necessary but, if ground, the TBZ will have the same efficacy as TBZ that has not been ground.

In another embodiment of the present invention there is provided yet another process for making an aqueous dispersion containing both DBDCB and TBZ comprising the steps of mixing water with effective amounts of sodium chloride, disodium EDTA and a block copolymer surfactant in a vessel fitted with a jacket and an agitator, adding an effective amount of a food grade, enzyme free xanthan gum to the mixture, adding an effective amount of anti-foam emulsion to the mixture and mixing until uniform, adding an effective amount of DBDCB to the mixture and mixing until uniform, cooling the mixture to a temperature of about 25° C., grinding the mixture, passing the ground mixture through a screen to remove gels or lumps, adding an effective amount of TBZ to the screened mixture and mixing until uniform. Again, in an alternative embodiment the TBZ can be added to the mixture before grinding.

In accordance with the present invention there is still further provided a method of inhibiting microbial growth comprising contacting said growth with an effective amount of a synergistic blend of DBDCB and TBZ as prepared by one of the processes recounted above. As used here, the term "effective amount" refers to that amount of a DBDCB/TBZ aqueous dispersion needed to achieve a desired level of inhibition of microbial growth.

The antimicrobial activity of the admixture of DBDCB and TBZ prepared by the methods described above has been confirmed using standard laboratory techniques. The dispersion has been found effective, for example, in inhibiting the growth of various bacterial and fungal strains including but not limited to Pseudomonas sp., *Alcaligenes facelis*, Enterobacter sp., *Aspergillus niger, Aureobasidium pullulans* and *Penicillium pinophilum*. Such bacteria and fungi are commonly found in paint and adhesive products. The aqueous dispersion blends prepared as described above have activity against these organisms when employed at appropriate levels of concentration. Those skilled in the art will understand that the required effective amount of the dispersion to use will vary with particular organisms and in particular applications. It will further be understood that many factors will determine the actual amount of the composition to be added in order to achieve the maximum amount of inhibition of microbial growth in a particular system. The determination of this amount is well within the skill of the artisan in this field.

Likewise, the amount of TBZ aqueous dispersion prepared according to the methods of the present invention which will effectively limit microbial growth will vary between systems and applications. Generally, however, for adhesives, the aqueous dispersion form of TBZ prepared as described herein can be added to the make-up water or as a post additive in adhesive production in amounts in excess of at least about 0.05, preferably ranging from about 0.1 to 5.0 weight percent of the 50% active formulation or at least about 0.1, preferably from about 0.2 to 10 weight percent of the 25% active formulation.

For interior and exterior coatings, the TBZ dispersion should be incorporated with the pigment grind. Typical formulations require at least about 0.1, preferably from about 0.20 to 4 pounds (lbs) of the 50% active product or at least about 0.1, preferably between about 0.40 to 8 lbs of the 25% active product, per 100 gallons of coating.

When used in the paper industry, TBZ is most effectively applied via the size tub, water trough, or coater. The TBZ dispersion should be added in an area of high agitation at a dosage of at least about 1.0, preferably from about 100 to 500 parts per million (ppm) for the 50% active product or at least about 2.0, preferably from about 200 to 1,000 ppm for the 25% active product, based on finished paper weight.

In production of canvas textiles, the fabric should be passed through a solution of the desired TBZ dispersion concentration, and should be applied at a dosage of at least about 10 ppm, preferably from about 250 to 1,500 ppm for the 50% active product or at least about 20 ppm, preferably from about 500 to 3,000 ppm for the 25% active product. Application of the TBZ dispersion in an effective quantity will provide mold and mildew resistance to canvas textiles.

For synthetic carpeting, when using spin finishing applications, at least about 0.01, preferably from about 0.05 to 0.2 weight percent of the 50% active product should be added, or from about 0.1 to 0.4 weight percent of the 25% active product should be used, based on the total weight of the material being used.

EXAMPLES

The following examples are provided to illustrate the invention in greater detail and should not be construed as limiting the scope of the present invention in any way.

Example I

Preparation of 25% by Weight Active DBDCB Dispersion

Table 1 represents the amount of each starting material used in preparation of approximately 1000 pounds of a DBDCB aqueous dispersion having an active concentration of about 25% by weight.

TABLE 1

| Name Of Item | Amount Of Raw Material Used Per 1000 Pounds Of Product (Pounds) |
| --- | --- |
| Zeolite Softened Water | 728.05 |
| Disodium EDTA (Edetic Acid, Disodium Dihydrate) | 1.00 |
| Sodium Chloride | 5.35 |
| Pluronic ® F-127 | 1.00 |
| Xanthan Gum (food grade, enzyme free) | 7.10 |
| Dow Corning ® Antifoam AF Emulsion | 2.50 |
| DBDCB Wet Cake (100% active basis) | 255.00 |

The Zeolite Softened Water was added to a stainless steel, jacketed tank fitted with an agitator and a Comitrol® high intensity grinder obtained from the Urschel Co. Agitation was initiated and the sodium chloride, disodium EDTA and Pluronic® F-127 were added to the tank and mixed until uniform, about five minutes. The xanthan gum, obtained from Kelco, was slowly added batchwise to the tank and mixed until dissolved; each batch of xanthan gum was allowed to disperse thoroughly before additional material was added. Addition of all of the xanthan gum took approximately 20 minutes. When addition of the xanthan gum was completed, the Antifoam AF Emulsion was added and mixed until dissolved, about 2 to 3 minutes. The temperature of the mixture was maintained at 25° C. by cooling the mixing tank jacket. The DBDCB Wet Cake was then added to the tank, and the mixture was allowed to agitate for approximately 15 minutes to ensure that all of the large lumps of DBDCB were broken up and a uniform slurry was formed. The slurry was then fed to the grinder operating in a recirculating mode. After grinding for approximately 10 minutes, a sample was withdrawn and screened through USS Nos. 100 and 200 mesh screens. This screening step was repeated until the slurry met the particle size specification as defined below. When this particle size was achieved the slurry was transferred to a second tank; during transfer the slurry was passed through a 10 mesh filter screen to remove any gels or lumps which were present. After transfer of the slurry from the first to the second tank, the grinder was shut off and the transfer lines purged into the second mix tank. This second tank was then agitated for about 30 minutes to blend the mixture.

The resulting product contained about 25.5% by weight DBDCB and had a wet particle size of about 0.25 maximum retained on USS No. 100 mesh and 97.5 minimum through USS No. 200 mesh. The Brookfield Viscosity of the dispersion was about 1850 cps as determined by a Brookfield RV viscometer operating with a #5 spindle at 50 revolutions per minute (rpm) and at 25° C.

Example II

Preparation of 25% by Weight Active TBZ Dispersion

Approximately one thousand pounds of a 25% by weight active TBZ dispersion were made using the following raw materials in the indicated amounts:

TABLE 2

| Name Of Item | Amount Of Raw Material Used Per 1000 Pounds Of Product (Pounds) |
|---|---|
| Zeolite Softened Water | 730.30 |
| Disodium EDTA | 1.00 |
| Sodium Chloride | 5.00 |
| Dow Corning ® Antifoam AF Emulsion | 2.50 |
| Xanthan Gum | 5.20 |
| DBDCB Wet Cake | 1.00 |
| Igepal ® CTA 639 | 5.00 |
| Thiabendazole, Dispersion Grade | 250.00 |

The water, which was at a temperature of about 27° C., was added to a stainless steel, jacketed tank fitted with a turbine-type agitator. Agitation was initiated and the disodium EDTA was added to the tank and mixed until dissolved, about 2 to 3 minutes. The sodium chloride was then added to the tank and mixed until dissolved, about 2 to 3 minutes. The Antifoam AF Emulsion was added to the tank and mixed until uniform, about 2 to 3 minutes. The xanthan gum, obtained from Kelco, was slowly added batchwise to the tank and mixed until dissolved; each batch of xanthan gum was allowed to disperse thoroughly before additional material was added. Addition of all of the xanthan gum took approximately 20 minutes. The mixture was allowed to agitate for approximately 30 minutes after all of the xanthan gum was added. The DBDCB, added as a preservative, was added to the mixture after the xanthan gum was completely mixed, and the tank agitated for about 2 to 3 minutes to dissolve the DBDCB. The Igepal® CTA 639 was then added to the tank and mixed until uniform, about 2 to 3 minutes. Thiabendazole (TBZ) was then added slowly to the tank over a period of approximately 30 minutes. Upon addition of all of the TBZ, the mixture was agitated for about one hour.

The resulting product had an active TBZ concentration of about 25% by weight. The Brookfield Viscosity of the product was approximately 1400 cps as determined with Brookfield RV viscometer using a #5 spindle at 50 revolutions per minute (rpm) and at 25° C.

Example III

Preparation of 50% by Weight Active TBZ Dispersion

Approximately one thousand pounds of a 50% by weight active ingredient TBZ dispersion were made as described above in Example II, but using the following raw materials in the indicated amounts:

TABLE 3

| Name Of Item | Amount Of Raw Material Used Per 1000 Pounds Of Product (Pounds) |
|---|---|
| Zeolite Softened Water | 482.10 |
| Disodium EDTA | 1.00 |
| Sodium Chloride | 5.00 |
| Dow Corning ® Antifoam AF Emulsion | 2.50 |
| Xanthan Gum | 3.40 |
| DBDCB Wet Cake | 1.00 |
| Igepal ® CTA 639 | 5.00 |
| Thiabendazole, Dispersion Grade | 500.00 |

Example IV

Preparation of an 80/20 DBDCB/TBZ 25% by Weight Active Aqueous Dispersion

An eight ounce sample of a DBDCB/TBZ 25% by weight active dispersion was prepared by adding about 6.4 ounces of a 25% by weight active DBDCB dispersion as prepared according to Example I and about 1.6 ounces of a 25% by weight active TBZ dispersion as prepared according to Example II to a mix tank and agitating the mixture with a turbine-type agitator until uniform. The active ingredients in the blend totalled approximately 25% by weight and the weight ratio of DBDCB to TBZ was about 80 to 20. The Brookfield viscosity of the blend was approximately 1600 cps as determined by a Brookfield RV viscometer using a #5 spindle at 50 rpm and at 25° C.

Example V

Efficacy of 80/20 DBDCB/TBZ 25% by Weight Active Dispersion

The following example demonstrates the biocidal efficacy, including preservation and mildew resistance, of a 25% by weight active dispersion of DBDCB/TBZ in a weight ratio of 80/20 as prepared according to Example IV.

Preservation Tests

Preservation tests were run on the DBDCB/TBZ dispersion by first placing 25 gram samples of various adhesives into separate containers. A ladder series of the 80/20 DBDCB/TBZ 25% by weight active biocide blend, prepared according to Example IV, in concentrations ranging from 0 ppm (control) to 2000 ppm, with the concentration in ppm being product based, was then added to the samples as indicated in the table below. The 25 gram adhesive samples were then inoculated with 0.25 milliliters (ml) of an inoculum containing equal amounts of four different gram negative bacteria (*Pseudomonas aeruginosa*, Pseudomonas sp., *Alcaligenes facelis*, and Enterobacter sp.) and having an overall organism concentration of $1 \times 10^6$. The samples were incubated at 30° C. and at 85% relative humidity. The samples were streaked on Tryptone Glucose Extract (TGE) agar twice—first after 2 days and again after 7 days. After streaking, the TGE agar plates were incubated at 30° C. and 85% relative humidity.

On the 7th day after the initial inoculation, the samples were inoculated a second time, again with 0.25 ml of the inoculum containing the four gram negative bacteria. The 25 gram samples were again incubated at 30° C. and at 85% relative humidity and streaked on TGE agar after 2 days and 7 days. After streaking, the TGE agar plates were incubated at 30° C. and 85% relative humidity. The TGE plates were read for bacterial growth every 7 days after streaking; this reading was performed by visual inspection. Results are recorded in the tables below and are based upon the following key: 0=no growth; 1=trace growth; 2=slight growth; 3=moderate growth; and 4=heavy growth.

TABLE 4

Flexible Ceramic Type Adhesive

| Concentration of biocide (ppm product based) | Concentration of biocide (grams) | Sample # | 1st Inoculation | | 2nd Inoculation | |
|---|---|---|---|---|---|---|
| | | | 2 days | 7 days | 2 days | 7 days |
| — | — | 1 | 4 | 4 | 4 | 4 |
| 250 | .0125 | 2 | 4 | 4 | 4 | 4 |
| 500 | .025 | 3 | 3 | 3 | 4 | 4 |
| 750 | .0375 | 4 | 2 | 2 | 4 | 4 |
| 1000 | .05 | 5 | 0 | 0 | 4 | 4 |
| 2000 | .1 | 6 | 0 | 0 | 4 | 4 |

TABLE 5

Easy Sanding Wall Patching Compound

| Concentration of biocide (ppm product based) | Concentration of biocide (grams) | Sample # | 1st Inoculation | | 2nd Inoculation | |
|---|---|---|---|---|---|---|
| | | | 2 days | 7 days | 2 days | 7 days |
| — | — | 1 | 4 | 4 | 4 | 4 |
| 250 | .0125 | 2 | 4 | 4 | 4 | 4 |
| 500 | .025 | 3 | 2 | 2 | 4 | 4 |
| 750 | .0375 | 4 | 1 | 1 | 4 | 4 |
| 1000 | .05 | 5 | 0 | 0 | 4 | 4 |
| 2000 | .1 | 6 | 0 | 0 | 4 | 4 |

TABLE 6

Smooth Patching Compound

| Concentration of biocide (ppm product based) | Concentration of biocide (grams) | Sample # | 1st Inoculation | | 2nd Inoculation | |
|---|---|---|---|---|---|---|
| | | | 2 days | 7 days | 2 days | 7 days |
| — | — | 1 | 0 | 0 | 4 | 4 |
| 250 | .0125 | 2 | 0 | 0 | 4 | 4 |
| 500 | .025 | 3 | 0 | 0 | 4 | 4 |
| 750 | .0375 | 4 | 0 | 0 | 4 | 4 |
| 1000 | .05 | 5 | 0 | 0 | 4 | 4 |
| 2000 | .1 | 6 | 0 | 0 | 0 | 0 |

As can be seen from the above tables, the 80/20 DBDCB/TBZ biocide blend was successful in eliminating organism growth in flexible ceramic type adhesive and easy sanding wall patching compound which had been subject to only one inoculation. Likewise, the blend eliminated microbial growth in the smooth patching compound after the second inoculation.

Mildew Resistance Tests

Mildew resistance tests were also carried out on various types of adhesives and one type of exterior vinyl paint. 50 gram aliquots of the paint were blended with a ladder series of 80/20 DBDCB/TBZ 25% by weight active dispersion in concentrations ranging from 0 ppm (control) to 2000 ppm as indicated in Table 7. The paint/biocide mixtures were then painted onto hard wood tongue blades, with two coats of the sample/dispersion mixture applied to each blade. The tongue blades were dried 24 hours between the first and second applications of the coats. Half of the painted tongue blades were subjected to weathering in a QUV Accelerated Weather Tester for 24 hours. The tongue blades were then inoculated with 1.0 ml of a mixed spore suspension containing equal amounts of *Aspergillus niger*, ATTC 6275, *Aureobasidium pullulans*, ATTC 9348, and *Penicillium pinophilum*, ATTC 9644; the overall organism concentration of the inoculum was $1\times10^6$. After inoculation, the tongue blades were incubated at 30° C. and 85% relative humidity. Mildew growth was recorded after 7 days and 14 days, and was read by visual inspection. The results are recorded in Table 7 below and are based on the following key: 0–3=heavy growth; 4–6=moderate growth; 7–9=trace growth; and 10=no growth.

ATTC 9644. The total organism concentration of the inoculum was $1\times10^6$. The samples were then incubated at 30° C. and 85% relative humidity. Reading was performed by visual inspection. Results were recorded after 7 days and 14 days as indicated in the tables below and are based on the following key: 0=no growth; 1=trace growth; 2=slight growth; 3=moderate growth; and 4=heavy growth.

TABLE 8

Easy Sanding Wall Compound

| Concentration of biocide (ppm) | Concentration of biocide (grams) | Sample # | Results 7 days | 14 days |
|---|---|---|---|---|
| — | — | 1 | 4 | 4 |
| 250 | 0.0125 | 2 | 4 | 4 |
| 500 | 0.025 | 3 | 4 | 4 |

TABLE 7

Exterior Vinyl Paint

| Concentration of biocide ppm Product Based | grams | Sample # | Mixed Spore Results 7 days Unweathered | Weathered | 14 days Unweathered | Weathered |
|---|---|---|---|---|---|---|
| — | — | 1 | 0 | 0 | 0 | 0 |
| 250 | .0125 | 2 | 0 | 0 | 0 | 0 |
| 500 | .025 | 3 | 0 | 0 | 0 | 0 |
| 750 | .0375 | 4 | 0 | 0 | 0 | 0 |
| 1000 | .05 | 5 | 0 | 0 | 0 | 0 |
| 2000 | .1 | 6 | 10 | 10 | 10 | 10 |

As is seen in Table 7, the 80/20 DBDCB/TBZ blend in concentrations of 2000 ppm eliminated all traces of microbial growth in weathered and unweathered specimens after both 7 and 14 days.

The adhesives were subjected to similar mildew resistance testing. 50 gram aliquots of 2 different adhesives were blended with a ladder series of 80/20 DBDCB/TBZ 25% by weight active dispersion in concentrating ranges from 0 ppm (control) to 2000 ppm as indicated in the tables below. Two coats of the adhesive/biocide mixture were painted onto Whatman #30 filter paper. Following the painting of the two coats of adhesive/biocide mixture on the paper, with 24 hours drying time between application of the coats, duplicate two inch squares of the coated paper were then placed on the surface of mineral salts agar (MSA) and then inoculated with 1.0 ml of a mixed spore suspension containing equal amounts of *Aspergillus niger*, ATTC 6275, *Aureobasidium pullulans*, ATTC 9348 and *Penicillium pinophilum*, TABLE 8-continued Easy Sanding Wall Compound

| Concentration of biocide (ppm) | Concentration of biocide (grams) | Sample # | Results 7 days | 14 days |
|---|---|---|---|---|
| 750 | 0.0375 | 4 | 4 | 4 |
| 1000 | 0.05 | 5 | 0 | 0 |
| 2000 | 0.1 | 6 | 0 | 0 |

TABLE 9

Smooth Packing Compound

| Concentration of biocide (ppm) | Concentration of biocide (grams) | Sample # | Results 7 days | 14 days |
|---|---|---|---|---|
| — | — | 1 | 4 | 4 |
| 250 | 0.0125 | 2 | 3 | 3 |
| 500 | 0.025 | 3 | 2 | 2 |
| 750 | 0.0375 | 4 | 1 | 2 |
| 1000 | 0.05 | 5 | 0 | 0 |
| 2000 | 0.1 | 6 | 0 | 0 |

As is seen in the above tables, the 80/20 DBDCB/TBZ blend at 1000 ppm eliminated microbial growth after 14 days in both the easy sanding wall compound and the smooth patching compound.

Example VI

Preparation of 80/20 DBDCB/TBZ 25% by Weight Active Dispersion

To prepare about 1000 pounds of an 80/20 dispersion of DBDCB/TBZ, 25% by weight active, the following amounts of raw materials should be used:

TABLE 10

| Name of Item | Amount of raw material per 1000 pounds of product (pounds) |
|---|---|
| Zeolite Softened Water | 728.05 |
| EDTA salt | 1.00 |
| Sodium Chloride | 5.35 |
| Surfactant | 1.00 |
| Xanthan Gum, food grade, enzyme free | 7.10 |
| Anti-foam agent | 2.50 |
| DBDCB | 204.00 |
| Thiabendazole, dispersion grade | 51.00 |

Add the Zeolite Softened Water to a stainless steel, jacketed tank fitted with an agitator and attached to a high intensity grinder. Initiate agitation and add the sodium chloride, a salt form of ethylenediaminetetraacetic acid and surfactant to the tank, mixing until uniform, about 5 minutes. Slowly add the xanthan gum batchwise and mix until dissolved; each addition off xanthan gum should be allowed to disperse thoroughly before additional material is added. Total addition of all of the xanthan gum should take about 20 minutes. When addition of the xanthan gum is completed, add the anti-foam agent and mix until dissolved, about 2 to 3 minutes. Maintain the temperature of the mix at about 25° C., such as through the use of jacket cooling the mixture. Add the DBDCB to the tank, and allow the slurry to agitate for approximately 15 minutes to ensure that all of the large lumps of DBDCB are broken up. Then add the TBZ and mix until uniform, about 20 minutes. The DBDCB/TBZ slurry should then be added slowly to the grinder, operating in a recirculating mode. Once a smooth, rapid flow of slurry is established, withdraw a sample and screen it through USS 100 and 200 mesh screens. This sample/screening step should be repeated until the slurry meets the particle size specification as defined below. When this is achieved, transfer the slurry to a second tank; during transfer, pass the slurry through a 10 mesh filter screen to remove any gels or lumps which are present. After transfer of the slurry from the first to the second tank, shut off the grinder and purge the transfer lines into the second mix tank. Agitate this second tank for about 30 minutes to blend the mixture. The resulting product should have about 20.4% by weight ±0.5 DBDCB, 5.0% by weight ±0.2 TBZ, a wet particle size of about 0.25 maximum retained on USS No. 100 and 97.5 minimum through USS No. 200 and a Brookfield Viscosity of between about 1600 and 2900 cps as determined with a #5 spindle at 50 revolutions per minute (rpm) and at 25° C.

What is claimed is:

1. A process for preparing a 2-(4-thiazolyl)-benzimidazole (TBZ) antimicrobial composition in aqueous dispersion form comprising the steps of:
   a. mixing an effective amount of xanthan gum with water in a vessel fitted with an agitator; and
   b. adding an effective amount of TBZ to the mixture of step (a) and mixing until uniform.

2. The process of claim 1 which further comprises:
   c. preparing a 1,2-dibromo-2,4-dicyanobutane (DBDCB) antimicrobial composition in aqueous dispersion form by
      i. mixing an effective amount of xanthan gum with water in a vessel fitted with an agitator;
      ii. adding an effective amount of (DBDCB) to the mixture of step (i) and mixing until uniform;
      iii. maintaining the mixture of step (ii) below a temperature of about 40° C.;
      iv. grinding the mixture of step (iii); and
   d. mixing a desired quantity of the TBZ antimicrobial composition with a desired quantity of the DBDCB antimicrobial composition to form an admixture containing both DBDCB and TBZ in aqueous dispersion form.

3. The process of claim 2 wherein the steps of preparing the TBZ and DBDCB antimicrobial compositions in aqueous dispersion form further include adding effective amounts of one or more processing aids selected from the group consisting of sodium chloride, salts of ethylenediaminetetraacetic acid (EDTA), a block copolymer surfactant, an antifoam agent and a wetting agent.

4. The process of claim 2 wherein the step of preparing the DBDCB antimicrobial composition further comprises passing the ground mixture of step (iv) through a screen to remove lumps or gels.

5. The process of claim 1 wherein steps a) and b) result in a dispersion comprising:
   a. between about 0.01 and 2% by weight xanthan gum;
   b. between about 0.1 and 60% by weight TBZ; and the balance water.

6. The process of claim 2 wherein steps a), b) and c) result in a dispersion comprising:
   a. between about 0.01 and 2% by weight xanthan gum;
   b. between about 0.1 and 60% by weight TBZ;
   c. between about 0.1 and 60% by weight DBDCB; and the balance water.

7. A process for preparing an aqueous dispersion of 1,2-dibromo-2,4-dicyanobutane (DBDCB) and 2-(4-thiazolyl)-benzimidazole (TBZ) comprising the steps of:
   a. mixing an effective amount of xanthan gum with water in a vessel fitted with an agitator;
   b. adding an effective amount of DBDCB to the mixture of step (a) and mixing until uniform;
   c. maintaining the mixture of step (b) below a temperature of about 40° C.;
   d. grinding the mixture of step (c);
   e. adding an effective amount of TBZ to the ground mixture of step (d); and
   f. mixing until uniform.

8. The process of claim 7 which further comprises: adding an effective amount of both DBDCB and TBZ to the mixture of step (a), and wherein step (e) is eliminated.

9. The process of claim 7 wherein steps a) through f) result in a composition comprising:
   a. between about 0.01 and 2% by weight xanthan gum;
   b. between about 0.1 and 60% by weight TBZ;
   c. between about 0.1 and 60% by weight DBDCB; and the balance water.

10. A process for preparing an aqueous dispersion of 1,2-dibromo-2,4-dicyanobutane (DBDCB) and 2-(4-thiazolyl)-benzimidazole (TBZ) which process comprises:

a. mixing water and effective amounts of sodium chloride, a salt form of ethylenediaminetetraacetic acid, and a surfactant in a vessel fitted with and agitator;

b. adding an effective amount of food grade, enzyme free xanthan gum to the mixture of step (a);

c. adding an effective amount of an antifoam emulsion to the mixture of step (b) and mixing until uniform;

d. adding an effective amount of DBDCB to the mixture of step (c) and mixing until uniform;

e. cooling the mixture of step (d) to a temperature of about 25° C.;

f. grinding the mixture of step (e);

g. passing the ground mixture through a screen to remove gels or lumps;

h. adding an effective amount of TBZ to the ground mixture of step (g); and i. mixing until uniform.

11. The process of claim 10 which further comprises: adding an effective amount of both DBDCB and TBZ to the mixture of step (c), and wherein step (h) is eliminated.

* * * * *